US008333695B2

(12) United States Patent
Cuschieri

(10) Patent No.: US 8,333,695 B2
(45) Date of Patent: Dec. 18, 2012

(54) MEDICAL INSTRUMENT AND METHOD FOR MANIPULATING, IN PARTICULAR RETRACTING TISSUE OR AN ORGAN

(75) Inventor: Alfred Cuschieri, St. Andrews (GB)

(73) Assignee: University of Dundee (GB)

( * ) Notice: Subject to any disclaimer, the term of this patent is extended or adjusted under 35 U.S.C. 154(b) by 1491 days.

(21) Appl. No.: 11/610,164

(22) Filed: Dec. 13, 2006

(65) Prior Publication Data

US 2007/0135685 A1    Jun. 14, 2007

(30) Foreign Application Priority Data

Dec. 13, 2005  (EP) .................................... 05027241

(51) Int. Cl.
*A61B 1/32* (2006.01)
(52) U.S. Cl. .......................................... 600/201; 600/37
(58) Field of Classification Search ................ 600/9–15, 600/201–246; 128/897–899
See application file for complete search history.

(56) References Cited

U.S. PATENT DOCUMENTS

| 5,364,404 A | 11/1994 | Jaffe et al. ..................... 606/106 |
| 6,299,625 B1 | 10/2001 | Bacher .......................... 606/170 |
| 6,358,196 B1 | 3/2002 | Rayman ........................... 600/12 |
| 6,652,540 B1 * | 11/2003 | Cole et al. ..................... 606/153 |
| 6,770,081 B1 | 8/2004 | Cooper et al. ................. 606/130 |
| 7,766,810 B2 * | 8/2010 | Ohdaira ........................... 600/12 |
| 2004/0138621 A1 | 7/2004 | Jahns et al. .................... 604/173 |
| 2005/0143774 A1 * | 6/2005 | Polo .............................. 606/205 |

FOREIGN PATENT DOCUMENTS

| EP | 276 104 | 7/1988 |
| GB | 2 406 276 | 3/2005 |
| WO | 00/09021 | 2/2000 |
| WO | 2004/064645 | 8/2004 |

* cited by examiner

*Primary Examiner* — John Lacyk
*Assistant Examiner* — Carrie R Dorna
(74) *Attorney, Agent, or Firm* — St. Onge Steward Johnston & Reens LLC

(57) ABSTRACT

A medical instrument for manipulating, in particular retracting tissue or an organ in the human or animal body, comprises an elongated shaft having a distal portion introducible into the body, and at least one working element arranged at a distal end portion of the shaft for manipulating the tissue or organ. The at least one working element comprises at least one magnetically acting element producing a magnetic field for manipulating the tissue or organ. A method for manipulating, in particular retracting tissue or an organ uses the instrument.

17 Claims, 5 Drawing Sheets

MEDICAL INSTRUMENT AND METHOD FOR MANIPULATING, IN PARTICULAR RETRACTING TISSUE OR AN ORGAN

CROSS REFERENCE TO RELATED FOREIGN APPLICATION

This application claims priority of European patent application No. 05027241.8 filed on Dec. 13, 2005.

BACKGROUND OF THE INVENTION

The invention relates to a medical instrument for manipulating, in particular retracting tissue or an organ in the human or animal body.

The invention further relates to a method for manipulating, in particular retracting tissue or an organ in the human or animal body which uses a medical Instrument of the aforementioned type.

In surgical operations on patients, it is often necessary to manipulate tissue or organs during the accomplishment of surgical tasks. Such manipulations can consist in putting aside an organ or tissue in order to obtain an access to deeper lying tissue or organs on which the surgical task is to be accomplished, or in retracting tissue or an organ for a subsequent dissection of tissue, for example. In this sense, manipulating can involve any kind of moving, turning, displacing and in particular retracting tissue or organs.

In the prior art, numerous instruments exist for the purpose of manipulating tissue. Regardless of whether the surgical task is being performed using open techniques or a minimal-invasive access approach, the vast majority of such instruments employ two jaws arranged at a distal end of the shaft of the instrument, and the jaws are operated by the motion of handles arranged at the proximal end of the shaft which handles usually are configured in a scissors-grip arrangement. The jaws at the distal end of the shaft of the instrument have grasping faces opposite to each other which are inclined at an acute angle to each other when grasping tissue. Such a prior art medical instrument for manipulating tissue or organs is known from document WO 00/09021, for example.

The use of such known medical grasping instruments for manipulating tissue or organs in the human or animal body exhibits several drawbacks.

The surfaces of the jaws of the instrument usually employ raised sharpened features, e.g. teeth, in order to obtain traction on slippery tissue surfaces. Such features inevitably cause trauma to the tissue surfaces which they grasp.

The jaws exert pressure on the tissues which they are grasping. Such pressure may cause direct trauma to the surfaces and internal structures of the tissue. Also, since such pressures may occlude the vascular supply, the tissues may become traumatised through ischaemia.

Further, the pressure exerted on tissues is not evenly distributed, but tends to be much greater close to the apex of the angle formed by the jaws.

Furthermore, the presence of the grasping instruments in the surgical field may impede access to the tissues required to accomplish the surgical intent.

SUMMARY OF THE INVENTION

It is on object of the present invention to provide a medical instrument of the type mentioned at the outset which does not exhibit the above drawbacks, and which, in particular, allows a manipulation, in particular retraction of tissue or organs with no or least a lesser degree of traumatisation of the tissue or organs than the conventional instruments described above.

It is another object of the present invention to provide a method for manipulating tissue or an organ of the type mentioned at the outset in which such an improved medical instrument is used.

According to an aspect of the invention, a medical instrument for manipulating tissue or an organ in a human or an animal body is provided, comprising an elongated shaft having a distal portion introducible into the body, and at least one working element arranged at a distal end portion of the distal portion of the shaft for manipulating the tissue or organ, the at least one working element comprising at least one magnetically acting element producing a magnetic field for manipulating the tissue or organ.

According to another aspect of the invention, a method for manipulating tissue or an organ in a human or animal body is provided, comprising treating the tissue or organ with a magnetically acting substance, providing a medical instrument, comprising an elongated shaft having a distal portion introducible into the body, and at least one working element arranged at a distal end portion of the distal portion of the shaft for manipulating the tissue or organ, the at least one working element comprising at least one magnetically acting element producing a magnetic field for manipulating the tissue or organ, introducing at least the distal end portion of the shaft of the instrument through a natural or artificial opening in the body surface towards the tissue or organ, and approaching the at least one magnetically acting element to a surface of the tissue or organ such that the magnetically acting element interacts with the magnetically acting substance via a magnetic force by which the tissue or organ is manipulated.

The present invention is based on the concept to manipulate, in particular retract tissue or organs by magnetic forces which interact between the at least one working element at the distal end portion of the shaft and the tissue or organ to be manipulated which, prior to the manipulating action, is treated with a magnetically acting substance. The use of a magnetic force for manipulating tissue has the main advantage that the manipulation can be carried out with at least reduced contact between the tissue and the instrument thus avoiding or at least reducing traumata to the tissue.

It is to be noted that magnetic manipulation of tissue and organs as such is known from document U.S. Pat. No. 6,358,196 B1. However, differently from the present invention, the known technique does not use medical instruments having at least one magnetically acting element as working element at a distal end portion of the shaft, in order to produce the magnetic field, but produces the magnetic field outside the patient's body. The magnetic field interacts with the magnetically acting substance supplied to the tissue to be manipulated through the body surface. The magnetic field is generated around the patient by means of an upper magnetic pole which is spaced above the patient. This known technique has the disadvantage that it is difficult to apply the magnetic field to the magnetically-responsive tissue in a well defined manner, and, further, it is difficult to vary the magnetic force in order to manipulate the tissue or organ in the desired direction or by the desired amount.

In contrast, the medical instrument according to the invention allows a well-defined controllable manipulation of tissue or organs by the fact that the magnetic field is produced at the distal end portion of the shaft of the instrument and thus close to the tissue or organ to be manipulated. As a result, the spatial expansion of the magnetic field can be made much smaller, and the zone of magnetic interaction with the tissue or organ is well-defined. A further advantage is that the magnetic field strength can be much lower because of the small distance between the at least one magnetically acting element of the instrument and the tissue or organ to be manipulated, than it is the case when the magnetic field is generated outside the patient's body in a greater distance from the tissue or organ.

In a preferred refinement of the medical instrument, the at least one magnetically acting element is a permanent magnet.

The advantage of this refinement is that a structurally simple instrument is provided which can be manufactured on a low-cost basis. The permanent magnet preferably is made of a ferromagnetic material.

In particular in combination with the afore-mentioned refinement, it is further preferred, if the at least one magnetically acting element is rod-shaped, or, also preferred, the at least one magnetically acting element is a toroidal magnet.

In particular, rod-shaped permanent magnets are widely available on the market and can be implemented in the instrument according to the invention without sophisticated manufacturing and production techniques.

In another preferred refinement, the at least one magnetically acting element is an electromagnet, in particular a current-driven coil.

The advantage of using an electromagnet in the medical instrument according to the invention is that the strength of the magnetic field produced by the electromagnet can be easily adjusted by controlling the current applied to the electromagnet. By controlling the strength of the magnetic field it is then possible to control the magnetic force which is responsible for the desired manipulation (motion) of the tissue or organ. The instrument can advantageously comprise a handpiece for adjusting the current applied to the electromagnet.

In a further preferred refinement, the at least one magnetically acting element is a magnetic dipole.

A magnetic dipole has the advantage that it establishes a well defined magnetic field axis defined by the two poles of the magnetic dipole. In connection with further preferred refinements to be explained below it is possible to orient the magnetic field axis with respect to the tissue by additionally providing that the at least one magnetically acting element is mounted movably at the distal end portion of the shaft of the instrument.

Preferred examples of magnetic dipoles are the above-mentioned rod-shaped permanent magnet or the current-driver coil as an electromagnet.

According to another preferred refinement, the at least one magnetically acting element is movably arranged at the distal end portion of the shaft.

This refinement is particularly advantageous in connection with the afore-mentioned refinement, according to which the magnetically acting element is a permanent magnet in form of a magnetic dipole. For, by moving the at least one magnetically acting element, the position or orientation of the magnetic dipole axis can be changed, and, by changing the orientation of the magnetic dipole axis, the magnetic force interacting between the magnetically acting element and the magnetically-responsive tissue can be raised or lowered. For example, when the magnetic dipole axis is oriented such that it runs approximately parallel to the surface of the tissue, there is very low magnetic force between the tissue and the magnetically acting element. When the magnetic dipole axis is oriented such that it runs approximately perpendicular to the surface of the tissue, the magnetic force is maximum, thus a larger amount of retraction or displacement of the tissue or organ is obtained.

A further advantage of a movably arranged magnetically acting element is that it is also possible not only to adjust the magnetic force between the magnetically acting element and the tissue, but also the direction of action of the magnetic force without moving the instrument as a whole.

In the context of the afore-mentioned refinement, it is further preferred if the at least one magnetically acting element is movably mounted at the distal end portion of the shaft for movement in the longitudinal direction of the shaft and/or transverse to the longitudinal direction of the shaft.

These types of movements of the at least one magnetically acting element do not change the orientation of the magnetic dipole axis in case that the magnetically acting element is a magnetic dipole, but these movements in particular are suited to change the distance between the magnetically acting element and the surface of the tissue or for changing the location where the magnetic force has its maximum influence on the tissue or organ.

As an alternative or in combination with the afore-mentioned refinement, it is further preferred, if the at least one magnetically acting element is rotatably mounted at the distal end portion of the shaft for rotation about a rotation axis running through the magnetically acting element.

In this refinement, rotation of the magnetically acting element about a rotation axis running through the magnetically acting element can be used to adjust the orientation of the magnetic field axis, in particular when the magnetically acting element is a magnetic dipole in order to adjust the strength of the magnetic force interacting between the magnetically acting element and the tissue or organ to be manipulated as already mentioned above.

In the latter case, it is further preferred if the rotation axis is orientated at least approximately perpendicular to the longitudinal direction of the shaft and at least approximately perpendicular to the dipole axis of the magnetic dipole.

By virtue of such an orientation of the rotation axis it is possible to adjust the magnetic dipole axis in any desired position between a position in which the dipole axis is perpendicular to the surface of the tissue, and a position in which the dipole axis is parallel to the surface of the tissue or organ.

In a further preferred refinement, the at least one magnetically acting element is articulatedly mounted at the distal end portion of the shaft for pivoting about at least one pivot axis spaced apart from the magnetically acting element.

By such an arrangement of the at least one magnetically acting element at the distal end portion of the shaft of the instrument, a superposition of a movement of the at least one magnetically acting element in the longitudinal direction of the shaft, the transverse direction of the shaft and/or a rotation of the magnetically acting element with respect to the longitudinal direction of the shaft can be accomplished along with the advantage of a simple construction.

In this context, it is preferred if the at lease one magnetically acting element is arranged at a distal end of an articulated arm which is mounted to the shaft by the at least one pivot axis.

The articulated arm preferably has at least two pivot axis for obtaining more degrees of freedom of movement of the at least one magnetically acting element.

Preferably, the articulated arm is designed such that it can be brought into a straight position in prolongation of the shaft of the instrument to pass the distal end portion of the shaft through an access port through the body surface.

In connection with one of the afore-mentioned refinements, according to which the at least one magnetically acting element is movably arranged at the distal end portion of the shaft of the instrument, it is further preferred, if the instrument comprises an actuating device which is operatively connected with the at least one working element for moving the at least one magnetically acting element with respect to the shaft.

Such an actuating device which can be arranged at a handpiece at the proximal end of the shaft can be operated by the surgeon in order to move the at least one magnetically acting element inside the patient's body for manipulating the tissue or organ.

In a constructively simple refinement, the actuation device is operatively connected with the at least one working element through an elongated force transmission element movable with respect to the shaft in the longitudinal direction of the shaft.

These types of force transmission from an actuating device at the proximal end of the instrument to the working element at the distal end of the shaft is already known from the prior art grasping instruments and, thus, it is possible to fall back on long-time experiences with common mechanical actuating mechanisms.

In a further preferred refinement, the instrument comprises a plurality of magnetically acting elements.

In this refinement, the number of magnetically acting elements is enhanced, which exhibits the advantage that a larger area of tissue or a larger organ can be manipulated, because the plurality of magnetically acting elements produces, in total, a more expanded magnetic field. In particular, this refinement may be combined with one of the afore-mentioned refinements according to which the at least one magnetically acting element is movable, i.e. in the present refinement all magnetically acting elements are movable, preferably independently from one another. Thus, a total magnetic field or a plurality of single magnetical fields can be produced for any desired manipulation of the tissue or organ in terms of direction of manipulation, and/or amount (stroke) of manipulation.

In a further preferred refinement, at least one sensor is arranged at the distal end portion of the shaft for sensing a distance between the at least one magnetically acting element and the surface of the tissue or organ.

As already mentioned above, one of the main advantages of the present invention is that the medical instrument according to the invention renders it possible to manipulate tissue or organs in a contactless manner, namely by the magnetic interaction between the at least one magnetically acting element and the tissue. The at least one sensor now has the advantage that the distance between the at least one magnetically acting element and the surface of the tissue or organ can be monitored such that a minimum distance is not fallen below in order to avoid a contact between the magnetically acting element and the tissue. The sensor can be designed in any fashion, for example as an optically acting sensor.

In a further preferred refinement, the at least one sensor is a magnetically sensitive sensor.

This matter is advantage that the sensor can use the magnetical field produced by the at least one magnetically acting element in order to produce a distance signal for monitoring the before-mentioned distance, thus resulting in a simpler construction.

The signal produced by the at least one sensor can be used, for example, to move the magnetically acting elements as described above in case that the at least one magnetically acting element is movably arranged at the distal end portion of the shaft.

Preferably, the at least one sensor produces an output signal for controlling the actuating device mentioned above.

In a refinement of the method according to the invention, the magnetic force interacting between the magnetically acting elements and the magnetically acting substance by which the tissue or organ to be manipulated is treated, is an attractive force.

It is further preferred, if the magnetically acting substance is a substance magnetizable in the magnetic field produced by the at least one magnetically acting element.

Such a magnetizable substance can be made, for example, of iron particles suspended in a liquid medium.

It is to be noted that the substance can also be a permanently magnetized material, e.g. a ferromagnetic substance.

In a further preferred refinement, the step of treating the tissue or organ includes applying the magnetically acting substance onto a surface of the tissue or organ.

There are known tissue glues which adhere to organic tissue, and in which, for example, iron particles are suspended in order to obtain a magnetically acting substance. To circumvent potential biocompatibility problems with the iron content of the adhesive, the adhesive must be confined to regions of the tissue which are to be surgically excised.

Another preferred refinement of the method includes injection of the magnetically acting substance into the tissue organ, or implanting or embedding magnetically-responsive pieces like wires, webs, clips, for example, into or onto the tissue or organ.

In a further preferred refinement of the method, the method comprises the step of controlling a direction and/or strength of the magnetic force between the at least one magnetically acting element and the tissue or organ.

In case that the magnetically acting element is movable with respect to the shaft as described above, the controlling of the direction and/or strength of the magnetic force includes moving the at least one magnetically acting element with respect to the shaft, as already explained above.

When the at least one magnetically acting element is an electromagnet, the controlling of the direction and/or strength of the magnetic force preferably includes controlling the current through the electromagnet as explained above.

Further, a distance between the at least one magnetically acting element and the surface of the tissue or organ is monitored so as to maintain at least a minimum distance.

In order to carry out the monitoring, the above-mentioned distance sensor can be used in order to obtain an automatically monitored and controlled distance.

Further advantages and features will become apparent from the following description and the accompanying drawings.

It is to be understood, that the afore-mentioned features and those features yet to be explained below are not only applicable in the given combinations, but also in other combinations or in isolation without departing from the scope of the invention.

BRIEF DESCRIPTION OF THE DRAWINGS

Exemplary embodiments will be described hereinafter with reference to the accompanying drawings, in which.

DETAILED DESCRIPTION OF PREFERRED EMBODIMENTS

Figure 1:
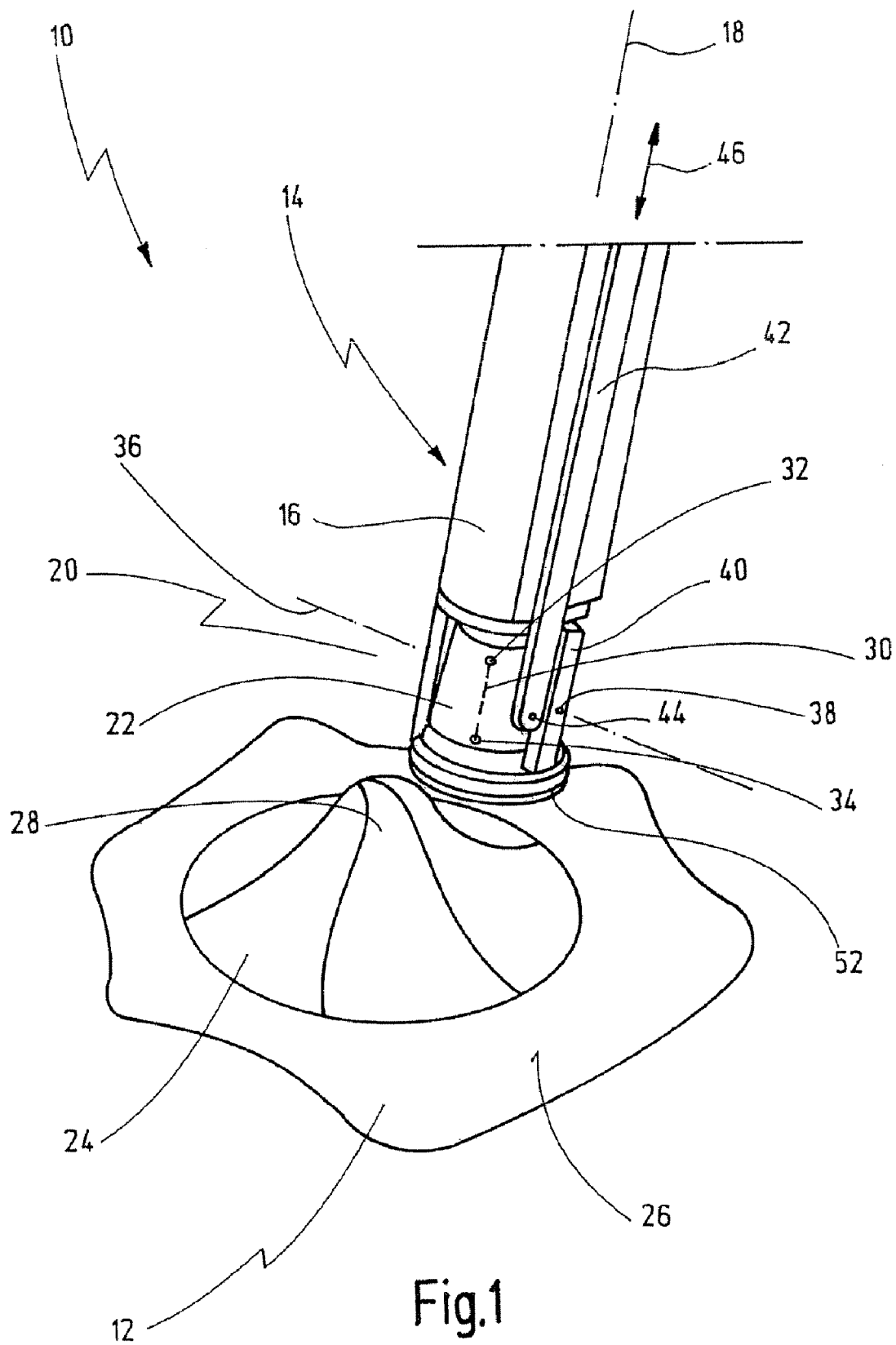
FIG. 1 shows a distal portion of a medical instrument according to a first embodiment in a perspective view.

FIG. 1 shows a distal portion of a medical instrument generally labelled with reference numeral 10. The medical instrument 10 may be used in open or minimal-invasive surgery for manipulating, in particular retracting tissue or an organ 12.

The medical instrument 10 comprises an elongated shaft 14, a distal end portion 16 of which is shown in FIG. 1 only. The shaft 14 defines a longitudinal axis 18. The shaft 14 may be straight or may have one or more curvatures over its length.

The distal end portion 16 of the shaft 14 is the part of the instrument 10 which is at least introducible into the human or animal body.

The medical instrument 10 comprises at least one working element 20, and in the present embodiment of FIG. 1 exactly one working element 20. The working element 20 is arranged at the distal end portion 16 of the shaft 14. The tissue 12 can be manipulated by means of the working element 20.

The working element 20 comprises at least one magnetically acting element 22, in the present embodiment exactly one magnetically acting element 22. The magnetically acting element 22 is a permanent magnet which produces a magnetic field for manipulating the tissue or organ 12.

In order to enable a magnetic interaction between the magnetically acting element 22 of the instrument 10 and the tissue or organ 12, the tissue or organ 12 has been treated with a magnetically acting substance 24 which in the present case has been applied on to a surface 26 of the tissue or organ 12. The magnetically acting substance 24 is a substance which is magnetizable in the magnetic field produced by the magnetically acting element 22. The magnetically acting substance 24 is, for example, a cyanoacrylate tissue glue in which iron particles have been suspended at a concentration of 10% by weight, for example.

The magnetically acting element 22 in form of a permanent magnet produces a magnetic field with a strength of between about 1 and about 1.5 Tesla, for example.

It is to be understood that the shaft 14, in particular the distal end portion 16 of the shaft 14 and other parts of the instrument 10 in the vicinity of the magnetically acting element 22 are not magnetically responsive.

By virtue of the magnetic field produced by the magnetically acting element 22, the magnetically acting substance 24 and, thus, the tissue or organ 12 is attracted toward the magnetically acting element 22, but preferably without coming into contact with the magnetically acting element 22 as will be described in more detail below.

FIG. 1 shows that a portion 28 of the tissue or organ 12 which is covered by the magnetically acting substance 24 is somewhat lifted or, in other words, retracted by the magnetic attractive force generated by the magnetically acting element 22.

In the present embodiment, the magnetically acting element 22 is rod-shaped. In particular, the magnetically acting element 22 is a magnetic dipole, defining a magnetic dipole axis 30 illustrated in FIG. 1 by a dashed line. Reference numeral 32 and 34 denote magnetic poles of the magnetically acting element 22, wherein, for example, pole 32 is the "north (N)" pole and pole 34 is the "south (S)" pole.

The magnetically acting element 22 is movably arranged at the distal end portion 16 of the shaft 14 so that the strength of the magnetic force acting on the magnetically acting substance 24 and, thus, on the tissue or organ 12 is adjustable.

In particular, the magnetically acting element 22 is rotatably mounted for free rotation about a rotation axis 36 which runs through the magnetically acting element 22, in the present embodiment through the centre of the magnetically acting element 22. The rotation axis 36 extends perpendicular to the magnetic dipole axis 30 and transverse to the longitudinal axis 18 of the shaft 14. To this end, the magnetically acting element 22 is mounted in a cage 40 attached to the distal end portion 16 of the shaft 14. The magnetically acting element 22 is articulatedly secured to the cage 40 by means of a joint 38. A force transmission element 42 which is axially movable in direction of the longitudinal axis 18 of the shaft 14, is articulatedly connected at 44 with the magnetically acting element 22 so that by an axial movement of the force transmission element 42 in one of the directions of a double arrow 46 the magnetically acting element 22 is rotated about the rotation axis 36.

The force transmission element 42 extends to a proximally arranged actuating device (not shown) for operation by the surgeon who uses the medical instrument 10. An example of a mechanical actuating device will be described in more detail below with reference to FIG. 6. By operating the actuating device which is operatively connected with the magnetically acting element 22 via the force transmission element 42, the magnetically acting element 22 is rotated about the rotation axis 36.

FIGS. 2a) through c) show the influence of the orientation of the magnetic dipole axis 30 on the strength of the magnetic force acting on the magnetically acting substance 24 and, thus, on the tissue or organ 12.

FIG. 2a) shows the situation where the magnetic dipole axis 30 is oriented parallel to the surface 25 of the magnetically acting substance 24 or the surface 26 of the tissue or organ 12. With this orientation of the magnetic dipole axis 30, there is no resulting magnetic force acting on the magnetically acting substance 24 and, thus, on the tissue or organ 12.

FIG. 2b) shows the situation where the force transmission element 42 has been pushed forward according to an arrow 48 so that the magnetically acting element 22 is rotated by an angle of about 45° with respect to FIG. 2a) so that the magnetic dipole axis 30 is inclined with respect to the surface 26 of the tissue or organ 12 leading to a magnetic attractive force retracting the magnetically acting substance 24 and, thus, the tissue or organ 12 towards the magnetically acting element 22 by a certain amount. With an orientation of the magnetic dipole axis 30 as shown in FIG. 2b), the magnetic attractive force, however, is not maximum.

FIG. 2c) shows the situation, where the magnetic attractive force is maximum for a given distance between the magnetically acting element 22 and the surface 25 of the magnetically acting substance 24. The maximum magnetic attractive force is obtained when the magnetic dipole axis 30 is oriented perpendicular to the surface 25 of the magnetically acting substance 24 as shown in FIG. 2c).

Thus, by controlling the orientation of the magnetic dipole axis 30 of the magnetically acting element 22, the strength of the magnetic force can be controlled.

A sensor is provided at the distal ends of the distal end portion 16 of the shaft 14 for sensing the distance between the magnetically acting element 22 and the surface 25. An automatic feedback control can be provided for the force transmission element 42 which automatically controls, by an axial movement of the force transmission element 42, the orientation of the magnetic dipole axis 30 with respect to the surface 25 in order to adjust the magnetic attractive force acting on the surface 25. An undesired contact between the surface 25 and the magnetically acting element 22 can be avoided in this way.

Avoiding a contact between the magnetically acting element 22 and the surface 25 can also be achieved by providing a non-magnetic spacer element which is permeable to the magnetic field produced by the magnetically acting element 22 and which is arranged, for example, at the position of the sensor 52 in FIG. 2a), and which avoids a contact between the magnetically acting element 22 and the surface 25 of the magnetically acting substance 24.

The sensor 52 preferably is a magnetically sensitive sensor, which senses the distance between the magnetically acting element 22 and the surface 25 by sensing the magnetic field between the magnetically acting element 22 and the surface 25.

As mentioned before, the sensor 52 preferably produces an output signal for controlling the force transmission element 42 for rotating the magnetically acting element 22 about the rotation axis 36.

Figure 3:
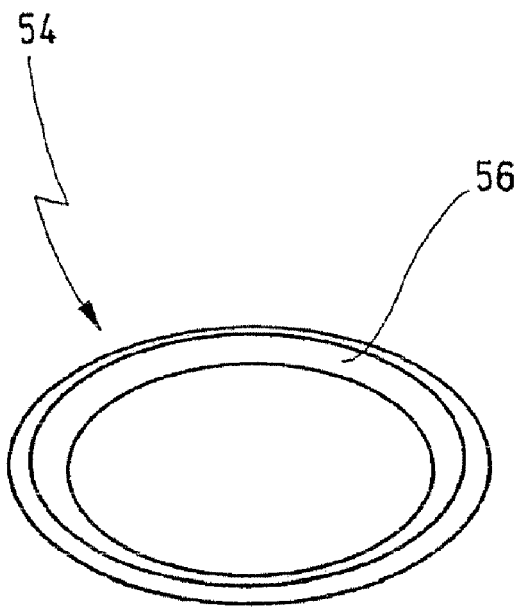
FIG. 3 shows a magnetically acting element in isolation according to another embodiment.

FIG. 3 shows another embodiment of a magnetically acting element 54 which is designed as a toroidal magnet 56. The toroidal magnet 56 can be used with the instrument 10 instead of the magnetically acting element 22.

Figure 4:
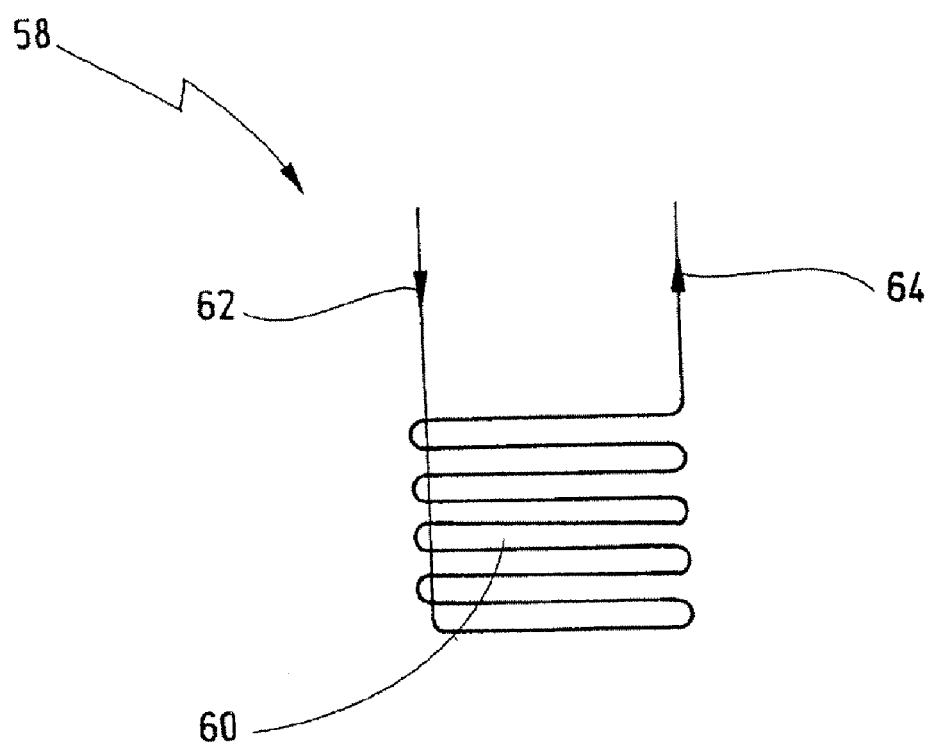
FIG. 4 shows a magnetically acting element in isolation according to still another embodiment.

FIG. 4 shows another embodiment for a magnetically acting element 58 which is an electromagnet, in the present embodiment a current-driven coil 60. The coil 60 can also be used with the instrument 10 instead of the magnetically acting element 22. The strength of the magnetic field produced by the current-driven coil and, thus, the magnetic force acting on the tissue or organ 12 can be controlled by controlling the current (indicated by arrows 62 and 64) through the coil 60. In this case, it is not necessary to arrange the coil 60 movably at the distal end portion 16 of the shaft 14 of the instrument 10, while a movable arrangement can also be envisaged.

Figure 5:
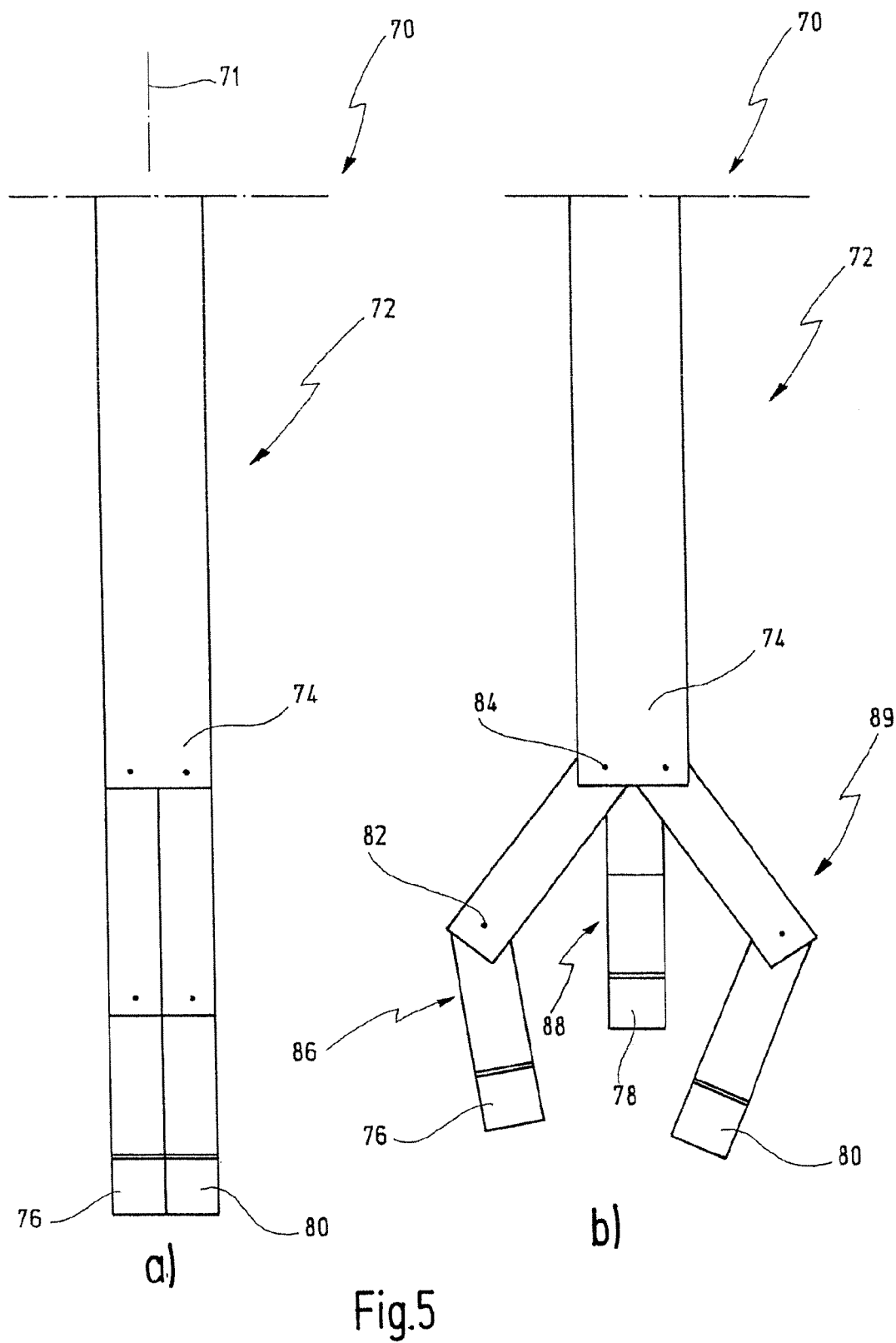
FIGS. 5a) and b) show a distal portion of a medical instrument according to another embodiment in two operational states.

FIG. 5a) and b) show another embodiment of a medical instrument 70 for manipulating tissue or an organ, comprising a shaft 72 having a distal end portion 74. The instrument 70 differs from the instrument 10 in that it comprises more than one magnetically acting elements arranged at the distal end portion 74 of the shaft 72. In more detail, there are three magnetically acting elements 76, 78, 80 which are located at 120.degree.intervals around the longitudinal axis of the shaft 72. Each of the magnetically acting elements 78, 78 and 80 is articulatedly mounted at the distal end portion 74 of the shaft 72 for pivoting about two pivot axes 82 and 84 as indicated for the magnetically acting element 76. The pivot axes 82 and 84 are spaced apart from the magnetically acting element 76, and the same holds for the magnetically acting elements 78 and 80 with their respective pivot axes. More than two pivot axes can be provided for each of the magnetically acting elements 76, 78 and 80.

The magnetically acting elements 76, 78 and 80 are each arranged at the distal end of an articulated arm 86, 88 and 89, wherein each arm 86, 88, 89 comprises the afore-mentioned pivot axes.

The arms 86, 88, 89 can be collapsed as shown in FIG. 5a) so that the distal end of the instrument 70 can be introduced through an access port in the body surface of a patient.

Each of the magnetically acting elements 76, 78, 80 produces a magnetically field, which fields superimpose to a total magnetic field covering a larger area of the tissue. The magnetically acting elements 76, 78, 80 are, in the present embodiment, rod-shaped permanent magnets similar to the magnetically acting element 22 of instrument 10. The magnetic force can be varied by pivoting the magnetically acting elements 76, 78, 80 starting from their position in FIG. 5a) into a position as shown in FIG. 5b), for example. By pivoting the magnetically acting elements 76, 78 and 80 about the pivot axes 82, 84 and the other pivot axis, the elements 76, 78 and 80 carry out motions in the direction of the longitudinal axis 71 of the shaft and transverse to the longitudinal axis 71 of the shaft 72. Thus, it is also possible with the instrument 70 to control the strength of the magnetic force acting on the tissue or organ.

It could also be envisaged to movably arrange the at least one magnetically acting element 22 of the instrument 10 or the elements 76, 78, 80 of the instrument 70 at the distal end of the shaft 14, 72 such that the magnetically acting elements, rather than be rotatable or pivotable, can carry out pure translatory movements in the direction of the shaft axis and/or transverse to the shaft axis.

Further, the magnetically acting element 54 and/or 58 in FIGS. 3 and 4 can also be used with the instrument 70 instead of the magnetically acting elements 76, 78 and 80, and it can also be envisaged to provide two magnetically acting elements or more than three magnetically acting elements at the distal end of the instrument 70.

Figure 6:
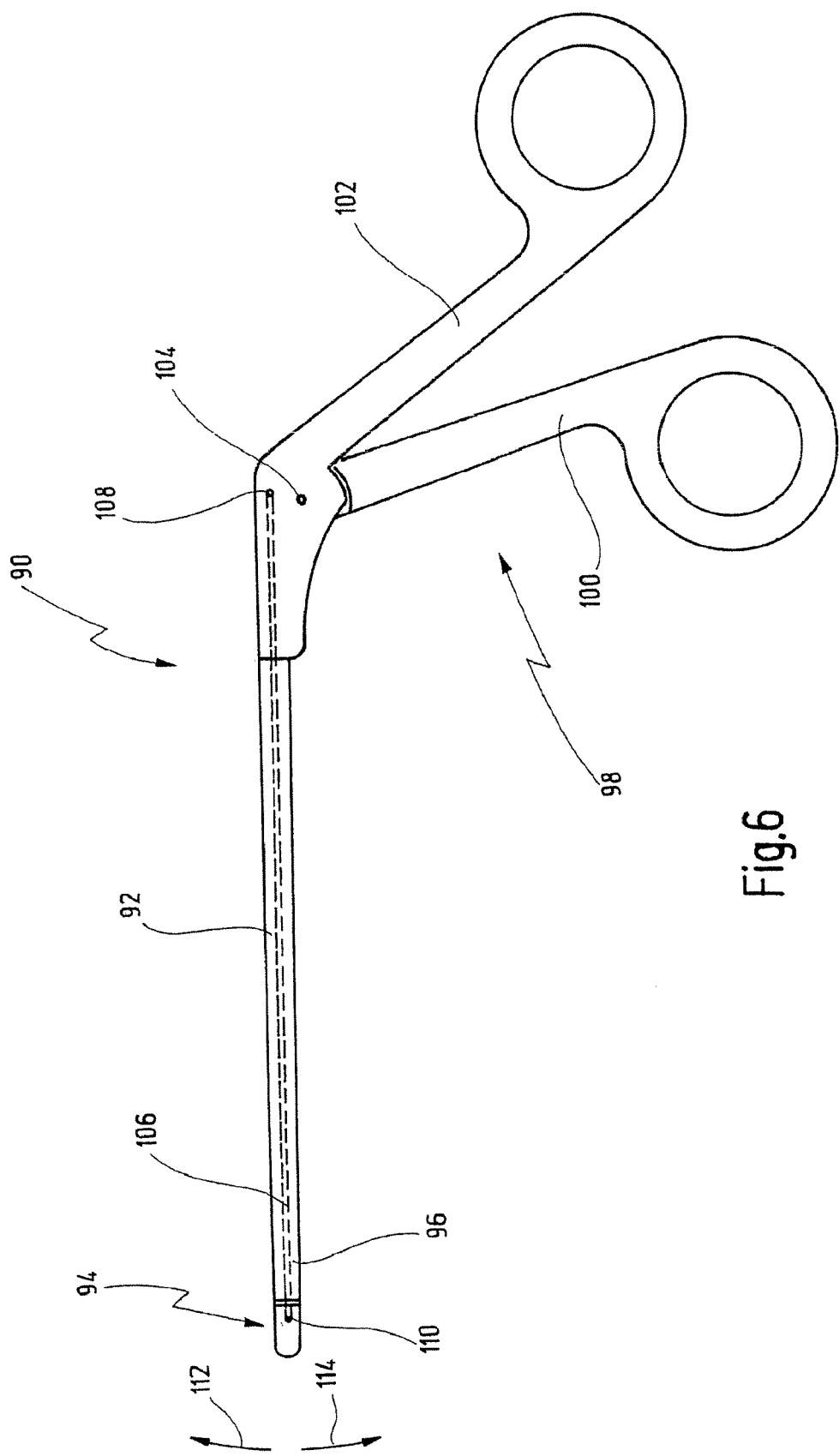
FIG. 6 shows a medical instrument in total according to still another embodiment.

FIG. 6 shows another embodiment of a medical instrument 90 for manipulating, in particular retracting tissue or organs in the human or animal body.

The instrument 90 comprises an elongated shaft 92, a magnetically acting element 94 at a distal end portion 96 of the shaft 92, and an actuating device 98 at the proximal end of the shaft 92. The actuating device 98 is configured as a scissors-grip arrangement and comprises a movable grip part 100 and an immovable grip part 102. The movable grip part 100 is pivotable about a pivot axis 104 with respect to the immovable grip part 102.

Figure 2:
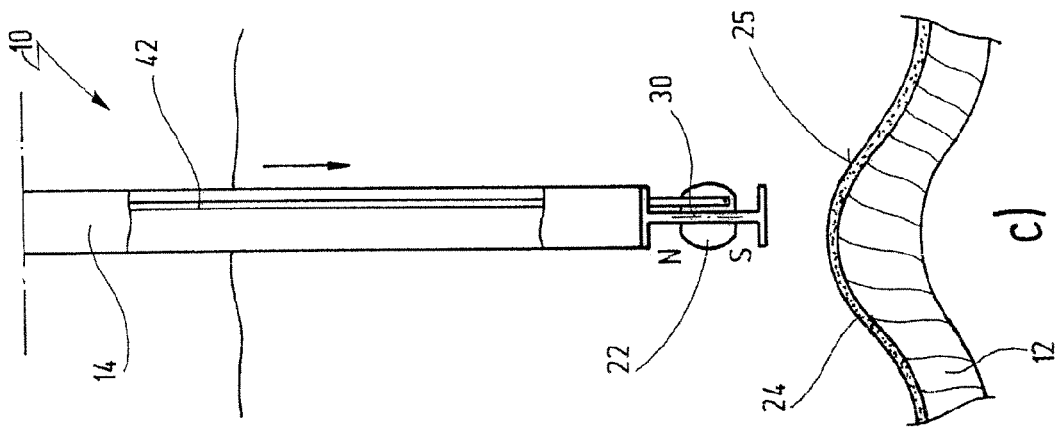
FIGS. 2a) through c) schematically show the instrument in FIG. 1 with different operational positions of the magnetically acting element.
Figure 2:
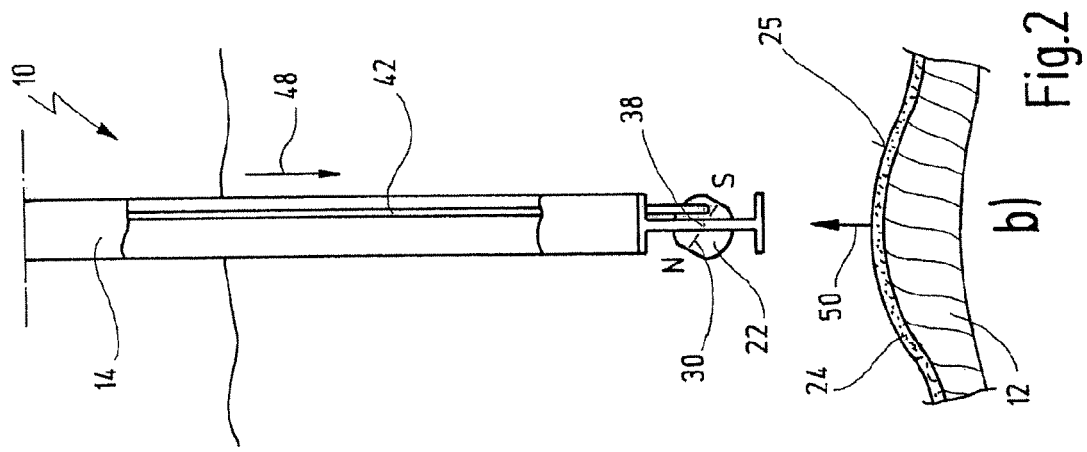
Figure 2:
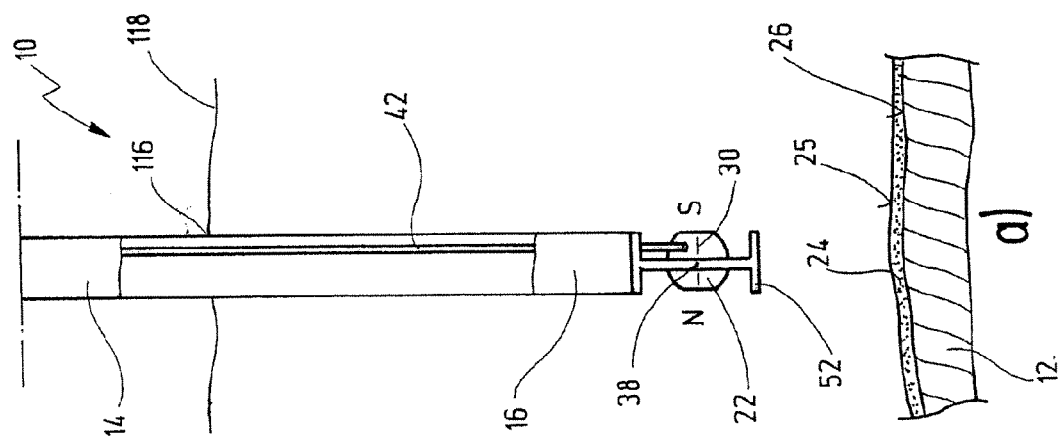

A force transmission element 106 is operatively connected at 108 with the movable grip part 100, and operatively connected at 110 with the magnetically acting element 94 which is movably, in particular rotatably mounted to the distal end portion 106 of the shaft 92 similar to the magnetically acting element 22 of instrument 10 in FIGS. 1 and 2. The magnetically acting element 94 produces a magnetic field for manipulating tissue or organs by a magnetic attractive force as described above with respect to FIG. 2. Arrows 112 and 114 show the directions of rotational movement of the magnetically acting element 94 when the movable grip part 98 is operated by the surgeon. The actuating device 98 is an example for a manually operable actuating device. Automatically controlled actuating devices which use the sensor 52, for example, as controller, are also conceivable.

Again with reference to FIG. 2, a method for manipulating, in particular retracting tissue or an organ in the human or animal body is described.

First, the tissue or organ 12 to be manipulated is treated with a magnetically acting substance 24 which in the embodiment shown in FIG. 2 is applied to the surface 26 of the tissue or organ 12.

The magnetically acting substance is, for example, a cyanoacrylate tissue glue in which iron particles have been suspended, preferably at a concentration of 10% by weight.

Other embodiments of treating the tissue or organ 12 with a magnetically acting substance include injecting the magnetically acting substance into the tissue or organ 12, for example liposome magnetite ($Fe_3O_4$) nanoparticles (these are super-paramagnetic) in suspension delivered by direct injection into the tissue or organ 12.

Another embodiment for treating the tissue or organ 12 with a magnetically acting substance includes embedding wires or clips of ferromagnetic metals into the tissue or organ 12. Such substances may be covered with a more biocompatible material, such as titanium, if it is intended that the substance is to remain in the tissue or organ 12.

Next, the instrument 10 is provided and introduced, at least with the distal end portion 16 of the shaft 14 through a natural or artificial opening 116 in the body surface 118 towards the tissue or organ 12 to be manipulated.

The at least one magnetically acting element 22 is approached to the surface 26 of the tissue or organ 12 such that the magnetically acting element 22 interacts with the magnetically acting substance 24 via a magnetic force by which the tissue or organ 12 can be retracted as shown in FIG. 2b) or FIG. 2c).

During manipulation of the tissue or organ 12, a direction and/or strength of the magnetic force between the at least one magnetically acting element 22 and the tissue or organ 12 is controlled.

In the embodiment shown in FIG. 2, the magnetically acting element 22 is movable, in particular rotatable, and the controlling of the direction and/or strength of the magnetic force then includes moving the magnetically acting element 22 with respect to the shaft 12.

In other embodiments, for example when an electromagnet as shown in FIG. 4 is used as the magnetically acting element, the controlling of the direction and/or strength of the magnetic force includes controlling the current through the electromagnet.

Further, the method includes monitoring a distance between the magnetically acting element 22 and the surface 26 of the tissue or organ 12 so as to maintain at least a minimum distance therebetween in order to avoid a contact between the tissue or organ 12 and the magnetically acting element 22.

It is to be understood that the features of the embodiments described above can be combined with one another or mutually exchanged.

What is claimed is:

1. A medical instrument for manipulating tissue or an organ in a human or an animal body, comprising:
   an elongated shaft having a distal portion introducible into said body, and at least one working element arranged at a distal end portion of said distal portion of said shaft for manipulating said tissue or organ, said at least one working element comprising at least one magnetically acting element producing a magnetic field for manipulating said tissue or organ;
   said at least one magnetically acting element being movably arranged at said distal end of said shaft;
   said at least one magnetically acting element being rotatably mounted at said distal end portion of said shaft for rotation about a rotation axis running through said at least one magnetically acting element;
   said rotation axis extending transverse to a longitudinal axis of the shaft;
   said at least one magnetically acting element having magnetic poles and the rotation axis of said at least one magnetically acting element being arranged between said magnetic poles;
   wherein rotation of the at least one magnetically acting element about the rotation axis changes the strength of a magnetic force acting between the at least one magnetically acting element and the tissue or organ.

2. The instrument of claim 1, wherein said at least one magnetically acting element is a permanent magnet.

3. The instrument of claim 1, wherein said at least one magnetically acting element is rod-shaped.

4. The instrument of claim 1, wherein said at least one magnetically acting element is a toroidal magnet.

5. The instrument of claim 1, wherein said at least one magnetically acting element is an electromagnet.

6. The instrument of claim 1, wherein said at least one magnetically acting element is a magnetic dipole.

7. The instrument of claim 1, wherein said at least one magnetically acting element is movably mounted at said distal end portion of said shaft for movement in a longitudinal direction of said shaft and transverse to said longitudinal direction of said shaft.

8. The instrument of claim 1, wherein said at least one magnetically acting element is a magnetic dipole, and said rotation axis is oriented at least approximately perpendicular to a longitudinal direction of said shaft and at least approximately perpendicular to a dipole axis of said magnetic dipole.

9. The instrument of claim 1, wherein said at least one magnetically acting element is articulatedly mounted at said distal end portion of said shaft for pivoting about at least one pivot axis spaced apart from said at least one magnetically acting element.

10. The instrument of claim 9, wherein said at least one magnetically acting element is arranged at a distal end of an articulated arm which is mounted to said shaft.

11. The instrument of claim 9, wherein said at least one magnetically acting element is pivotable about at least a second pivot axis.

12. The instrument of claim 1, further comprising an actuating device which is operatively connected with said at least one working element for moving said at least one magnetically acting element with respect to said shaft.

13. The instrument of claim 12, wherein said actuating device is operatively connected with said at least one working element through an elongated force transmission element movable with respect to said shaft in a longitudinal direction of said shaft.

14. The instrument of claim 12, wherein at least one sensor is arranged at said distal end portion of said shaft for sensing a distance between said at least one magnetically acting element and a surface of said tissue or organ, and said at least one sensor produces an output signal for controlling said actuating device.

15. The instrument of claim 1, comprising a plurality of magnetically acting elements.

16. The instrument of claim 1, wherein at least one sensor is arranged at said distal end portion of said shaft for sensing a distance between said at least one magnetically acting element and a surface of said tissue or organ.

17. The instrument of claim 16, wherein said at least one sensor is chosen from a group consisting of a magnetically sensitive sensor or an optical sensor.

* * * * *